United States Patent
Sanders et al.

(10) Patent No.: US 10,494,629 B2
(45) Date of Patent: Dec. 3, 2019

(54) RNA ISOLATION FROM SOLUBLE URINE FRACTIONS

(71) Applicant: Quest Diagnostics Investments LLC, Secaucus, NJ (US)

(72) Inventors: Heather Sanders, Winchester, CA (US); Hai-Rong Li, Mission Viejo, CA (US)

(73) Assignee: Quest Diagnostics Investments LLC, Secaucus, NJ (US)

(*) Notice: Subject to any disclaimer, the term of this patent is extended or adjusted under 35 U.S.C. 154(b) by 0 days.

(21) Appl. No.: 16/118,864

(22) Filed: Aug. 31, 2018

(65) Prior Publication Data
US 2019/0062726 A1 Feb. 28, 2019

Related U.S. Application Data

(63) Continuation of application No. 15/130,039, filed on Apr. 15, 2016, now Pat. No. 10,066,226, which is a continuation of application No. 12/973,747, filed on Dec. 20, 2010, now Pat. No. 9,315,802.

(60) Provisional application No. 61/290,976, filed on Dec. 30, 2009.

(51) Int. Cl.
*C12P 19/34* (2006.01)
*C12N 15/10* (2006.01)
*C12Q 1/6886* (2018.01)

(52) U.S. Cl.
CPC ....... *C12N 15/1017* (2013.01); *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 6,171,869 | B1 | 1/2001 | Safarian |
| 6,479,632 | B1 | 11/2002 | Wallach |
| 8,192,931 | B2 * | 6/2012 | Fradet ................ C12Q 1/6886 435/6.1 |
| 2005/0164223 | A1 * | 7/2005 | Schalken ............ C12Q 1/6886 435/6.14 |
| 2006/0183107 | A1 | 8/2006 | Melkonyan et al. |
| 2009/0239221 | A1 | 9/2009 | Chinnalyan et al. |
| 2010/0273148 | A1 | 10/2010 | Guilford et al. |
| 2011/0111976 | A1 | 5/2011 | Fare et al. |

OTHER PUBLICATIONS

Hanke et al., "Detailed Technical Analysis of Urine RNA-Based Tumor Diagnostics Reveals ETs2/Urokinase Plasminogen Activator to Be a Novel Marker for Bladder Cancer," Clinical Chemistry, vol. 53, No. 12, pp. 2070-2077, 2007.
Gertsch et al., "Relative Quantification of mRNA Levels in Jurkat T Cells with RT-Real Time-PCR (RT-rt-PCR): New Possibilities for the Screening of Anti-Inflammatory and Cytotoxic Compounds," Pharmaceutical Research, vol. 19, No. 8, pp. 1236-1243, Aug. 2002.
Heid et al., "Real time quantitative PCR," Genome Research, vol. 6, pp. 986-994, 1996.
Nolan et al., "Quantification of mRNA using real-time RT-PCR," Nat. Protoc., vol. 1, No. 3, pp. 1559-1582, 2006.
Rashtchian, "Amplification of RNA," PCR Methods Applic., vol. 4, pp. S83-S91, 1994.
Office Action dated Apr. 25, 2014 in U.S. Appl. No. 12/973,747.
Office Action dated Oct. 9, 2014 in U.S. Appl. No. 12/973,747.
Office Action dated May 5, 2015 in U.S. Appl. No. 12/973,747.
Office Action dated Sep. 22, 2015 in U.S. Appl. No. 12/973,747.
Notice of Allowance dated Dec. 14, 2015 in U.S. Appl. No. 12/973,747.
Office Action dated Jul. 20, 2017 in U.S. Appl. No. 15/130,039.
Office Action dated Jan. 16, 2018 in U.S. Appl. No. 15/130,039.
Notice of Allowance dated May 4, 2018 in U.S. Appl. No. 15/130,039.

* cited by examiner

*Primary Examiner* — Kenneth R Horlick
(74) *Attorney, Agent, or Firm* — Foley & Lardner LLP

(57) ABSTRACT

The invention provides methods for isolating RNA from the soluble fraction of urine. The methods can be used for detecting the presence or absence of an RNA, or quantifying the amount of an RNA. The methods are useful for diagnosing an individual suspected of having a disease by detecting the level of RNA associated with the disease in the soluble fraction of urine. The methods are also useful for prognosing an individual diagnosed with a disease by detecting the level of RNA associated with the disease in the soluble fraction of urine.

20 Claims, 2 Drawing Sheets

RNA ISOLATION FROM SOLUBLE URINE FRACTIONS

CROSS-REFERENCE TO RELATED APPLICATIONS

This application is a Continuation of U.S. application Ser. No. 15/130,039, filed Apr. 15, 2016, now issued U.S. Pat. No. 10,066,226, which is a Continuation of U.S. application Ser. No. 12/973,747, filed Dec. 20, 2010, now issued U.S. Pat. No. 9,315,802, which claims benefit of U.S. Provisional Application No. 61/290,976, filed Dec. 30, 2009.

FIELD OF THE INVENTION

This invention relates to methods for isolating, processing, and identifying nucleic acids from biological fluids.

SUMMARY OF THE INVENTION

The present invention relates to methods for extracting RNA from urine. In some embodiments, the a soluble urine concentrate is formed from the urine sample. In other embodiments, the urine sediment is removed from soluble urine concentrate. Optionally, the RNA is subsequently processed in order to determine the identity, presence, or amount of the RNA or the gene products encoded by that RNA, identify the cell type(s) from which the RNA originated, and/or to determine a diagnosis or prognosis for a pathological conditions indicated by the presence and/or identity of that RNA. Preferably, the RNA extracted from the soluble fraction of urine is mammalian RNA (e.g., non-viral RNA). Suitable mammalian urine sample include, for example, urine samples obtained from humans, horses, dogs, and cats. Optionally, the subject from which the urine sample is obtained has been previously diagnosed as having a pathological condition.

Generally, the methods provide for isolating RNA from the soluble fraction of urine from an individual (e.g., a patient) by concentrating the RNA in the urine sample to produce a soluble urine concentrate. The RNA may be subsequently isolated from the soluble urine concentrate or may be further processed without isolation. Optionally, the urine sediment may be separated from the soluble urine fraction prior to concentration. Alternatively, the urine sediment may be physically or functionally separated from the soluble urine fraction during the concentration step. Urine sediment that is functionally separated from the soluble urine fraction may be in physical contact with the soluble fraction but has been processed in such a manner that the contents of the sediment do not contribute to the RNA of the soluble fraction. For example, cells, organelles, other cellular debris, and insoluble matter (e.g., mineral crystals) may be pelleted from the urine sample by centrifugation and the sample further processed in order that the cells and organelles are not disrupted to either become resuspended in the soluble fraction or lysed to release nucleic acids contained therein into the soluble fraction. Alternatively, the urine sediment may be separated from the soluble fraction by filtration.

The RNA in the soluble urine fraction may be concentrated to form a soluble urine concentrate by any suitable means including, for example, ultrafiltration (e.g., using a filter membrane having a cutoff of about 100 kDa, 50 kDa, 10 kDa, or 3 kDa), lyophilization, dialysis, or other means for dehydration or concentration. In some embodiments, the soluble urine concentrate is formed by ultrafiltration of the soluble urine fraction through a membrane filter having a suitable molecular weight cutoff. Ultrafiltration may be performed using a syringe filter or a centrifugal filtration unit. In some embodiments, the membrane filter has a net positive or net neutral charge. Suitable membrane materials include, for example, cellulose based materials (e.g. regenerated cellulose, methylcellulose, cellulose triacetate), polysulfone, and polyethersulfone. Dialysis may be performed against any suitable counter-solvent including for, example, polyethylene glycol, and the dialysis membranes are designed to have any appropriate molecular weight cutoff, as described herein. In embodiments which use lyophilization to form the soluble urine concentrate, the urine sediment is physically separated from the soluble urine fraction prior to lyophilization. Optionally, the lyophilized product containing the RNA from the soluble fraction is resuspended (solubilized) following lyophilization in a volume of diluent less than the original volume of the urine sample. The RNA from the soluble urine concentrate may be isolated by any suitable method including, for example, solid phase extraction. Optionally, the RNA is subsequently released from the solid phase for further processing.

Specifically, in one aspect, the invention provides a method for isolating RNA from the soluble fraction of urine by: a) concentrating a urine sample to produce a soluble urine concentrate having RNA, and b) isolating RNA from the soluble urine concentrate.

In another aspect, the invention provides a method for determining the presence or amount of a target RNA in a urine sample, by isolating RNA from the soluble fraction of urine using any of the methods described herein, and using the isolated RNA in a hybridization-based assay to determine the presence or amount of the target RNA. Target RNA may be detected and/or quantified using any appropriate method including hybridization-based methods such as real-time PCR.

In another aspect, the invention provides a method for amplifying nucleic acids from a urine sample by a) concentrating the urine sample to produce a soluble urine concentrate, b) isolating RNA from the soluble urine concentrate produced in step (a), c) reverse transcribing the RNA from the soluble urine concentrate produced in step (b) to form cDNA; and d) amplifying the cDNA produced in step (c).

In any of these methods, optionally two or more RNAs or their corresponding cDNAs are detected and/or quantified.

Also provided are methods for determining a diagnosis or prognosis for an individual. The methods producing a soluble urine concentrate according to any of the methods provided herein and determining the presence or identity of the RNA, if any, in that soluble urine concentrate. For diagnosis, the amount of RNA (either total or of a specific type) is compared to a reference value (e.g., the amount of that RNA present in a healthy individual or an individual known to have the disease under investigation). For prognosis, the amount or type of the RNA may be compared to a reference value, wherein the reference value is referenced to either healthy individuals or individuals known to have specific disease outcomes. Exemplary diseases amenable to analysis by the methods described herein include, for example, prostate cancer, bladder cancer, uterine cancer, ovarian cancer, and cervical cancer. In one example, benign prostate hyperplasia may be diagnosed by assessing one or more urinary RNAs selected from the group consisting of heat shock 60 kDa protein (HSPD1), inosine monophosphate dehybrogenase 2 (IMPDH2), PDZ and LIM domain 5 (PDLIM5), and UDP-N-acteylglucosamine pyrophosphorylase 1 (UAP1).

In one example, the above methods further include detecting the RNA from the soluble urine concentrate. In one example of the above methods, the RNA is mRNA. Exemplary methods for detecting RNA include reverse transcription coupled with real-time PCR, northern blot, UV spectroscopy, hybridization of RNA or cDNA to a probe such as in microarray or flow cytometry.

Urine may be obtained from any individual. An individual may be healthy and without any known disease. Alternatively, an individual may be a person suspected of having a disease. Urine samples may be pooled from multiple individuals or from multiple samples obtained from a single individual. In the latter case, the combined sample may represent the total daily urinary output of a single individual. Preferably, urine samples are collected in sterile containers in order to minimize the possibility for contamination by environmental microorganisms or other foreign matter. In one embodiment, the urine sample is obtained using a catheter.

As used herein the term "soluble fraction of urine" means urine which is substantially free (less than about 1% w/w) of cells, cellular debris, organelles, organisms, and insoluble matter (e.g., mineral crystals). Typically, an unprocessed urine sample obtained from an individual is a mixture of the soluble fraction and the urine sediment, with the soluble fraction making up the largest portion of the mixture. Under normal conditions, the material that makes up the urine sediment is suspended in the soluble fraction and requires processing to effect useful separation. Preferably, the soluble fraction of urine and the resulting soluble urine concentrate are acellular (i.e., lacking cells). It is understood that the urine fraction may be rendered acellular (e.g., by filtration and/or centrifugation) without necessarily removing all other insoluble matter such as organelles, cellular debris, and insoluble matter.

As used herein the term "urine sediment" means that fraction of urine comprising cells, cellular debris, organelles, organisms, and/or insoluble matter that may be removed from the soluble fraction of urine. Exemplary methods for separating urine sediment from soluble fraction of urine include centrifugation, filtration, and/or sedimentation under gravity.

As used herein the term "soluble urine concentrate" means that soluble fraction of urine which is substantially free (less than about 1% w/w) of cells, cellular debris, organelles, and organisms and where the volume of the soluble fraction of urine has been reduced by at least 50%, at least 60%, at least 75%, at least 80%, at least 90% or more from the original urine volume.

As used herein the term "ultrafiltration" means a separation process which includes a filtration through a semi permeable membrane under a positive pressure such that solutes of higher molecular weight are retained by the membrane while water and low molecular weight solutes pass though the membrane. Exemplary positive pressure includes but not limited to hydrostatic pressure, centrifugal force.

As used herein the term "nominal molecular weight limit" in the context of a filter membrane means a pore size where over 90% of the solute with that molecular weight will be retained. Exemplary nominal molecular weight limit suitable for concentrating soluble urine fraction comprising RNA include 3 kDa, 10 kDa, 30 kDa, 50 kDa and 100 kDa.

The term "RNA" is meant to include mRNA, tRNA, and rRNA. In preferred embodiments, the RNA is mammalian RNA (e.g., RNA obtained from mammalian urine). In other embodiments, the RNA is non-viral.

"Primer" refers to an oligonucleotide that hybridizes to a substantially complementary target sequence and is capable of acting as a point of initiation of DNA synthesis when placed under conditions in which primer extension is initiated (e.g., primer extension associated with an application such as PCR). An oligonucleotide "primer" may occur naturally, as in a purified restriction digest or may be produced synthetically. Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. An optimal length for a particular primer application may be readily determined in the manner described in H. Erlich, PCR Technology, Principles and Application for DNA Amplification (1989).

A "probe" refers to an oligonucleotide that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of an RNA or cDNA in a sample by virtue of the sequence characteristics of the target. Probes can be labeled or unlabeled, or modified in any of a number of ways well known in the art. A probe may specifically hybridize to a target nucleic acid. Probes can be designed which are between about 10 and about 100 nucleotides in length and hybridize to the target nucleic acid such as RNA or cDNA. Oligonucleotides probes are preferably 12 to 70 nucleotides; more preferably 15-60 nucleotides in length; and most preferably 15-25 nucleotides in length. The probe may be labeled with a detectable label.

DETAILED DESCRIPTION OF THE INVENTION

Figure 1:
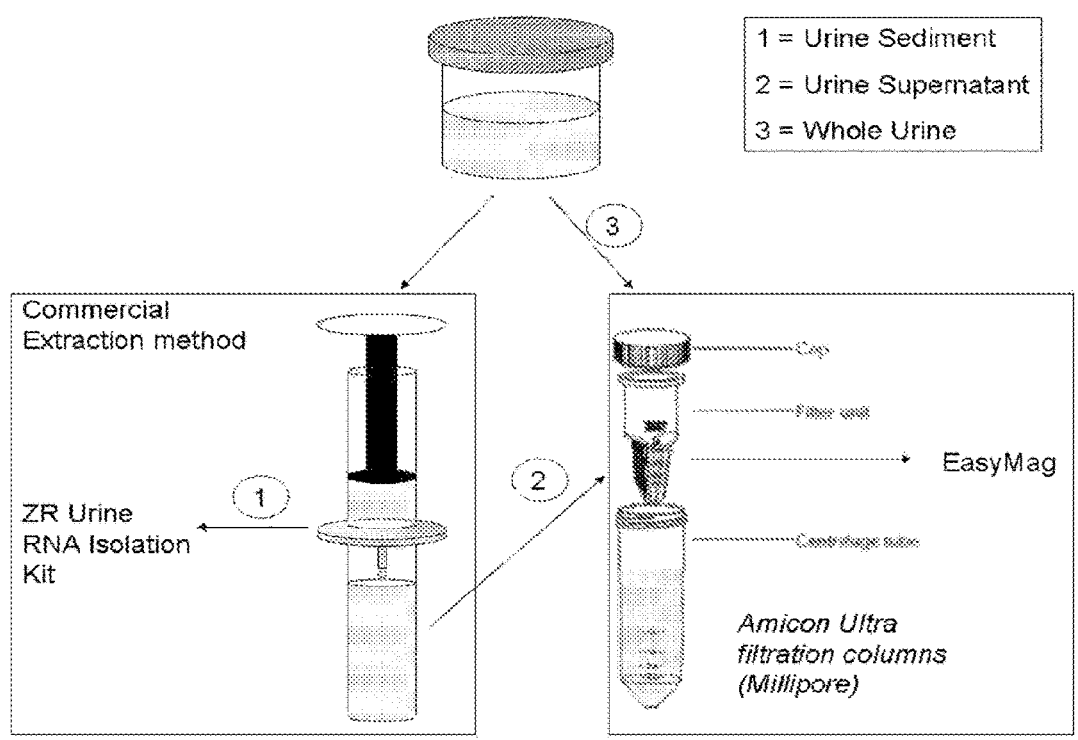
FIG. 1 shows a schematic of the experimental design of isolating RNA from urine sediment, urine filtrate (after removing cells from urine by filtration) and whole urine. Three different RNA isolation procedures are illustrated.

The present invention provides methods for isolating RNA from the soluble fraction of urine. Also provided are methods for detecting RNA in soluble fraction of urine and methods for diagnosis and prognosis by detecting RNA associated with a disease in soluble fraction of urine.

Sample

A urine sample typically consists of a soluble fraction and a sediment fraction. The sediment fraction may contain cells, cellular debris, organelles, microorganisms, and/or insoluble minerals (e.g., kidney stones). Soluble urine fraction is substantially free (less than 1% w/w) of urine sediment and preferably contains only soluble molecules (e.g., urea, nucleic acids, soluble proteins, etc.). Urine samples may be obtained from healthy individuals (i.e., free of known disease) or individuals known or suspected to have a disease or other condition. Alternatively, a urine sample may consist of urine samples pooled from several individuals.

Methods for Separating Urine Sediment From Soluble Urine Fraction

The urine sediment may be separated from the soluble urine fraction by any convenient method including, for example, centrifugation, sedimentation under gravity, or filtration. In one example, centrifugation can be performed at 1000× g to 30,000× g for 10 minutes to pellet the urine sediment and some or all of the soluble urine fraction may be removed. In another example, urine sediments can be separated by filtration using relatively high molecular weight cutoff filters such that the urine sediment is retained on the filter membrane while the soluble urine fraction including the soluble RNA passes into the filtrate. Exemplary filter membranes can be made of cellulose based membranes (e.g. regenerated cellulose, methylcellulose, cellulose triacetate), polysulfone, polyethersulfone. Commercial kits such as ZR Urine RNA Isolation Kit™ (ZYMO Research Corporation) are available to remove urine sediments from soluble urine fraction.

Methods for Concentrating Soluble Urine Fractions

Soluble urine fractions may be concentrated by any convenient method suitable for the volume of urine to be processed and the anticipated size of the soluble RNA to be identified and isolated. Suitable concentration methods include, for example, ultrafiltration, lyophilization, and dialysis (e.g., against polyethylene glycol). Ultrafiltration, involves filtration though a semi permeable membrane under a positive pressure such as hydrostatic pressure or centrifugal force such that solutes of higher molecular weight remain in the retentate while water and low molecular weight solutes pass into the filtrate. Typically, the membranes used for concentration have a smaller pore diameter (e.g., lower molecular weight cutoff) than the filters used to remove the urine sediment.

Preferably, the semipermeable membrane materials used for concentrating soluble urine fractions do not bind or retain soluble RNA. Suitable materials include, for example, cellulose based materials (e.g. regenerated cellulose, methylcellulose, cellulose triacetate), polysulfone, and polyethersulfone. The semipermeable membranes are available in various pore sizes. The pore size where over 90% of the solute with that molecular weight will be retained is termed as "nominal molecular weight limit" (NMWL). Exemplary nominal molecular weight limits suitable for isolating RNA from urine include 3 kDa, 10 kDa, 30 kDa, 50 kDa and 100 kDa. The pore size of semipermeable membranes include nominal molecular weight limits that can range from about 1 kDa to about 200 kDa, from about 2 kDa to about 150 kDa, and from about 3 kDa to about 100 kDa. Table 1 below provides general guidance for selecting the membrane for retention of RNA based on the nucleotide content of a nucleic acid. Alternatively, the soluble RNA is retained on the filter and later recovered. Suitable membranes for soluble RNA retention include anionic membranes such as PVDF.

TABLE 1

NMWL guidelines for selecting semipermeable membrane for ultrafiltration.

| NMWL | Single-stranded nucleotide cut-off (bases) | Double-stranded nucleotide cut-off (base pair) |
| --- | --- | --- |
| 3 kDa | 10 | 10 |
| 10 kDa | 30 | 20 |
| 30 kDa | 60 | 50 |
| 50 kDa | 125 | 100 |
| 100 kDa | 300 | 125 |

Various commercially available ultrafiltration kits and devices are available to concentrating a sample such as Amicon Ultra-4 Centrifugal Filter Units, Amicon Ultra-15 Centrifugal Filter Units, Centricon® centrifugal filter devices (Millipore, Mass., USA), Pierce Concentrator (Thermo Fisher Scientific, IL, USA). In one example, 15 ml of soluble urine fraction can be concentrated to 500 µl using Amicon Ultra-15 Centrifugal Filter Units by centrifugation for 30 minutes at 4000× g.

In one example, soluble urine fraction can be concentrated by lyophilization. Lyophilization is a freeze-drying process that works by freezing the material and then reducing the surrounding pressure and adding enough heat to allow the frozen water in the material to sublime directly from the solid phase to gas. Lyophilization machines are available from commercial vendors such as Labconco (MO., USA), Millrock Technology (NY, USA).

In another example, soluble urine fraction can be concentrated by placing the soluble urine fraction by dialysis against a solution containing polyethylene glycol and using a dialysis bag with appropriate molecular cutoff. The molecular weight cutoff can range from 3 kDa-100 kDa depending on the size of RNA to be retained within the dialysis bag. Appropriate dialysis tubings can be obtained commercially such as Sigma-Aldrich, Thermo-Scientific.

Methods for RNA Isolation and Extraction

RNA may be isolated and extracted from aqueous samples such as soluble urine fraction or soluble urine concentrate using standard techniques, see, e.g., Sambrook, et al., Molecular Cloning: A Laboratory Manual, Second Edition (1989), Cold Spring Harbor Press, Plainview, N.Y. Particularly useful are solid phase extraction methods. Reagents and kits for isolating RNA from a biological sample are commercially available e.g., RNeasy Maxi Kit, RNeasy Protect Mini kit, RNeasy Protect Cell Mini kit, QIAamp RNA Blood Mini kit, from Qiagen; MELT™, RNaqueous®, ToTALLY RNA™, RiboPure™-Blood, Poly(A)Purist™ from Applied Biosystems; TRIZOL® reagent, Dynabeads® mRNA direct kit from Invitrogen. In one example, kits provided by Qiagen employ silica resin to bind nucleic acid including RNA. RNA in the solution binds to the silica resin while the proteins and other solutes passes through. After several steps of washing, RNA can be eluted using the buffer provided by the manufacturer. In one example, NucliSENS® easyMAG® automated system (bioMérieux, Inc., NC, USA) may be used for the extraction of total nucleic acids including RNA. RNA from soluble urine fraction or soluble urine concentrate will bind to NucliSENS® magnetic silica particles. The RNA bound to the magnetic silica particles will be washed with wash buffer supplied by the manufacturer and will be eluted from the magnetic silica particles by heating using manufacturer's protocol. In another example, RNA can be isolated by adsorbing on an anion exchange resin followed by elution with high salt buffer. Exemplary anion exchange resins include Diethylaminoethyl (DEAE) crosslinked to polystyrene or cellulose, DNAPac® series of polymer-based anion-exchange columns from Dionex, anion exchange columns from Thermo Scientific.

Reverse Transcription of RNA to cDNA

Various methods to reverse transcribe RNA to cDNA are known in the art. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus Thermophilus*. In one example, RNA extracted from soluble urine fraction or soluble urine concentrate may be reverse transcribed to cDNA using the protocol adapted from the Superscript II Preamplification system (Life Technologies, GIBCO BRL, Gaithersburg, Md., catalog no: 18089-011), as described by Rashtchian, A., PCR Methods Applic. (1994), 4: S83-S91. The method is described below.

One (1) to five (5) micrograms of RNA extracted from soluble urine fraction or soluble urine concentrate in 13 μl of DEPC-treated water is added to a clean microcentrifuge tube. One microliter of either oligo (dT) (0.5 mg/ml) or random hexamer solution (50 ng/μl) is added and mixed gently. The mixture is then heated to 70 degrees centigrade for 10 minutes and then incubated on ice for one minute. Then, it is centrifuged briefly followed by the addition of 2 μl of 10× Synthesis buffer (200 mM Tris-HCl, pH 8.4, 500 mM KCl, 25 mm magnesium chloride, 1 mg/ml of BSA), 1 μl of 10 mM each of dNTP mix, 2 μl of 0.1 M DTT, 1 μl of SuperScript II RT (200 U/μl) (Life Technologies, GIBCO BRL, Gaithersburg, Md.). After gentle mixing, the reaction is collected by brief centrifugation, and incubated at room temperature for 10 minutes. The tube is then transferred to a 42° C. water bath or heat block and incubated for 50 minutes. The reaction is then terminated by incubating the tube at 70° C. for 15 minutes, and then placing it on ice. The reaction is collected by brief centrifugation, and 1 μl of RNase H (2 units) is added followed by incubation at 37° C. for 20 minutes before proceeding to nucleic acid amplification.

In another example, reverse transcription of RNA to cDNA was combined with the RT-PCR reaction using RNA UltraSense® one-step real-time (RT) PCR System (Invitrogen).

Detection of RNA

The presence or amount of RNA isolated from soluble urine fraction or soluble urine concentrate can be determined by several methods known in the art. In one example, RNA can be detected by Northern blot. See, e.g., Sambrook, et al., Molecular Cloning: A Laboratory Manual, Second Edition (1989), Cold Spring Harbor Press, Plainview, N.Y. In another example, RNA can be detected by reverse transcription coupled with PCR, including real-time PCR. The cDNA is amplified in a real-time PCR reaction using gene specific primers. Real-time PCR detects the copy number of PCR templates such as cDNA in a PCR reaction. Exemplary methods for quantification of RNA by real-time PCR is described by Nolan et al. (Nat Protoc. 2006; 1(3): 1559-82) and Gertsch et al. (Pharm Res. 2002 August; 19(8): 1236-43). The references are incorporated herein by reference. In another example, RT-PCR is performed in a combination with a reverse transcription of RNA to cDNA reaction using RNA UltraSense® one-step real-time (RT) PCR System (Invitrogen).

In one example, amplification of cDNA is monitored by SYBR green dye. The dye binds to double-stranded (ds) DNA in PCR, causing fluorescence of the dye. An increase in DNA product during PCR therefore leads to an increase in fluorescence intensity and is measured at each cycle, thus allowing DNA concentrations to be quantified.

In another example, amplification of cDNA is monitored by TaqMan® probes (Heid et al., Genome Res. 1996; 6: 986-994). TaqMan® probes are based on the principle of fluorescence quenching and involve a donor fluorophore and a quenching moiety. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency than it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), TAMRA, 4-(4-dimethylaminophenylazo) benzoic acid (DABCYL), and the ATTO-series of quenchers (ATTO 540Q, ATTO 580Q, and ATTO 612Q; Atto-Tec GmbH). TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye. If the quencher is an acceptor fluorophore, then accumulation of PCR product can be detected by monitoring the decrease in fluorescence of the acceptor fluorophore.

To ensure accuracy in the quantification, it is usually necessary to normalize expression of a target gene to one or more reference genes that are stably expressed. Exemplary reference genes include beta actin (ACTB), beta-2 microglobulin (B2M), glyceraldehyde-3-phosphate dehydrogenase (GAPDH). Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, Ct. A lower Ct value indicates higher copy number of an RNA. Amounts of RNA is determined by comparing the results to a standard curve produced by real-time PCR of serial dilutions of a known amount of RNA or DNA.

Detection by Hybridization. RNA isolated from soluble urine fraction or soluble urine concentrate can be detected following reverse transcription and amplification by hybridization with a nucleic probe that hybridizes specifically to the RNA of interest (i.e., a target RNA). The methods of the present invention can incorporate all known methods and means and variations thereof for carrying out DNA hybridization, see, e.g., Sambrook, et al., 1989, Molecular Cloning: A Laboratory Manual, Second Edition, Cold Spring Harbor Press, Plainview, N.Y.

The RNA or cDNA may form a complex on a solid support prior to being detected. The complex may comprise a capture probe anchored to a solid support, the RNA of interest hybridized to the capture probe, and a detectably labeled probe hybridized to the RNA of interest. In some cases, the solid support may comprise a first member of a binding pair and the capture probe may comprise a second member of the binding pair. The binding of the first member of the binding pair to the second member of the binding pair may anchor the capture probe to the solid support. Examples of solid support include but are not limited to beads, microparticles, microarray plates, microwells. Examples of binding pair include but are not limited to biotin/streptavidin, ligand-receptor, hormone-receptor, and antigen-antibody.

RNA and/or cDNA can be detected by performing an array-based hybridization to detect the genes of interest in a sample, or to diagnose a disease in an individual. The resolution of array-based method is primarily dependent upon the number, size and map positions of the nucleic acid elements within the array, which are capable of hybridizing to the RNA. Microarrays are available commercially that cover all human genes. For example, GeneChip® Human Exon 1.0 ST Array from Affymetrix (CA, USA), Whole Human Genome Microarray Kit from Agilent Technologies (CA, USA) are capable of evaluating gene expression of all known transcripts in human.

Alternatively, the hybridized complexes can also be detected using flow cytometry. Flow cytometry is a technique well-known in the art. Flow cytometers hydrodynamically focus a liquid suspension of particles (e.g., cells or synthetic microparticles or beads) into an essentially single-file stream of particles such that each particle can be analyzed individually. Flow cytometers are capable of measuring forward and side light scattering which correlates with the size of the particle. Thus, particles of differing sizes may be used in invention methods simultaneously to detect distinct nucleic acid segments. In addition fluorescence at one or more wavelengths can be measured simultaneously. Consequently, particles can be sorted by size and the fluorescence of one or more fluorescent labels probes can be analyzed for each particle. Exemplary flow cytometers include the Becton-Dickenson Immunocytometry Systems FACSCAN. Equivalent flow cytometers can also be used in the invention methods.

RNA Associated With Disease

RNA isolated from soluble urine fraction or soluble urine concentrate may be associated with a disease and can be useful for diagnosis and prognosis of such disease. The RNA associated with a disease may be overexpressed or underexpressed in a disease condition. Detecting the level of RNA may be indicative of the diagnosis and prognosis of the disease. Exemplary RNA associated with a disease that can be isolated from soluble urine fraction or soluble urine concentrate by the methods of the present invention are shown in Table 2 below.

TABLE 2

RNA associated with disease

| Disease | Gene Name | Symbol | GenBank Accession No. | Reference |
|---|---|---|---|---|
| Prostate Cancer | Prostate cancer antigen 3 | PCA3 | NR_015342 | Mearini et al. Biomarkers. 2009; 14(4): 235-43<br>Schalken et al., Urology. 2003; 62(5 Suppl 1): 34-43<br>Tinzl et al. Eur. Urol. 2004; 46(2): 182-6 |
| Prostate Cancer | P antigen family, member 4 | PAGE4 | NM_007003 | Iavarone et al. Mol Cancer Ther. 2002; 1(5): 329-35<br>Kong et al. Hepatogastroenterology. 2004; 51(59): 1519-23 |
| Prostate Cancer | Solute carrier family 45, member 3 | SLC45A3 | NM_033102 | Sheridan et al. Am J Surg Pathol. 2007; 31(9): 1351-5 |
| Prostate Cancer | Kallikrein-related peptidase 3 | KLK3 | NM_001030047 | Mabjeesh et al. Prostate. 2009; 69(11): 1235-44 |
| Ovarian Cancer | Phosphoinositide-3-kinase, catalytic, alpha polypeptide | PIK3CA | NM_006218 | Kadota et al. Cancer Res. 2009; 69(18): 7357-65) |
| Ovarian Cancer | Erythroblastic leukemia viral oncogene homolog 2 | ERBB2 | NM_001005862 | Tong et al. BJOG. 2009; 116(8): 1046-52 |
| Bladder Cancer | Hyaluronoglucosaminidase 1 | HYAL1 | NM_007312 | Eissa et al. Cancer. 2005; 103(7): 1356-62 |
| Bladder Cancer | Bladder cancer associated protein | BLCAP | NM_001167820 | Yao et al. Mol Cell Biochem. 2007; 297(1-2): 81-92 |
| Bladder Cancer | Solute carrier family 35, member E3 | SLC35E3 | NM_018656 | Clark et al. Genome Res. 2003; 13(10): 2265-70 |
| Bladder Cancer | Tumor protein p53 | TP53 | NM_000546 | Ouerhani et al. Cancer Invest. 2009; 27(10): 998-1007 |

TABLE 2-continued

RNA associated with disease

| Disease | Gene Name | Symbol | GenBank Accession No. | Reference |
|---|---|---|---|---|
| Uterine Cancer | P antigen family, member 4 | PAGE4 | NM_007003 | Iavarone et al. Mol Cancer Ther. 2002; 1(5): 329-35 Kong et al. Hepatogastroenterology. 2004; 51(59): 1519-23 |
| Cervical Cancer | Suppressor of tumorigenicity 20 | ST20 | NM_001100879 | Kim et al. Int J Cancer. 2002 Feb. 20; 97(6): 780-6 |

The references and the sequences of the RNA associated with a disease are incorporated herein by reference.

Example 1

Detection of RNA from Large Volume of Liquid Sample

The ability to detect RNA in a large volume of liquid sample was tested by adding 5 µl of RNA (845.6 ng/µl) to 15 ml of Tris-EDTA (TE) buffer. The resulting RNA solution was concentrated to less than 500 µl by centrifugation using Amicon Ultra-15 filter units with nominal molecular weight limit of 3 kDa and 10 kDa (Millipore, Mass., USA). The concentration of RNA in the retentate from two different membrane filters were determined using NanoDrop™ spectrophotometer (Thermo Scientific), which requires small volume of sample for analysis. The recovery of RNA were comparable from the two membrane filter types: 94% for 10 kDa and 100% for 3 kDa. The results are shown in Table 3 below.

TABLE 3

Retention of spiked cell line RNA in TE measured by Nanodrop concentration.

| Sample | Volume (µl) | Conc. (ng/µl) | Total (ng) | % Recovery |
|---|---|---|---|---|
| Spiked RNA/15 ml TE | 5 | 845.6 | 4228 | |
| 10 kDa membrane retentate | 160 | 24.9 | 3984 | 94% |
| 3 kDa membrane retentate | 270 | 15.7 | 4239 | 100% |

Example 2

Comparison of Recovery of Spiked RNA from Membranes with Different Pore Sizes The range of filter pore sizes that can be used to concentrate the RNA were evaluated for RNA retention using filter columns ranging from 3 kDa-100 kDa. A known amount of cell line RNA (34 g) was spiked into a large volume of TE buffer (75 ml), split into five aliquots for a starting amount of 6.8 µg of total RNA per 15 ml aliquot. Each 15 ml aliquot was concentrated through five separate filter columns with different pore sizes (nominal molecular weight limit: 3 kDa, 10 kDa, 30 kDa, 50 kDa and 100 kDa retention, respectively). After concentration with the filter columns, the % recovery was determined. First, RNA yield was calculated by multiplying the final volume of sample by the final concentration of the sample measured by nanodrop. Second, the RNA yield was divided by the starting amount of RNA (6.8 µg) to give the final % recovery of each filter column. Based on these results, the 3 kDa pore size gave the highest recovery of 94%, followed by 10 kDa (87%), 30 kDa (78%), 50 kDa (80%), and 100 kDa with the lowest and final yield (67%). The results are shown in Table 4 below.

TABLE 4

Retention of spiked cell line RNA in TE measured by Nanodrop concentration.

| Sample | Volume (µl) | Conc. (ng/µl) | Total (ng) | % Recovery |
|---|---|---|---|---|
| Spiked RNA/15 ml TE | 5 | 1360 | 6800 | |
| 100 kDa membrane retentate | 135 | 33.7 | 4550 | 67% |
| 50 kDa membrane retentate | 206 | 26.4 | 5438 | 80% |
| 30 kDa membrane retentate | 290 | 18.4 | 5336 | 78% |
| 10 kDa membrane retentate | 190 | 31.3 | 5947 | 87% |
| 3 kDa membrane retentate | 428 | 15.0 | 6420 | 94% |

Example 3

Comparison of Recovery of Endogenous Urine RNA from Membranes with Different Pore Sizes Some factors may effect the efficiencies in retention of RNA in a real sample with endogenous RNA versus a sample spiked with RNA. These factors include the presence of partially degraded or fragmented RNA and the presence of urine RNases that may degrade RNA prior to processing. The ability of membranes with different pore sizes to retain endogenous urine RNA was evaluated. Whole urine (75 ml) was obtained from five separate donors and split into five 15 ml aliquots per donor. Each of the five aliquots per donor was concentrated using the filters of five different pore sizes (nominal molecular weight limit: 3 kDa, 10 kDa, 30 kDa, 50 kDa, and 100 kDa). RNA from each sample of concentrated urine was extracted using EasyMag. Amplification of two different transcripts (GAPDH and ABL1) was performed for each sample by RT-PCR. In order to quantitate retention efficiencies, RNA concentrated from the top performing filter column in the RNA spiking studies (3 kDa) was used as the baseline (100%) for each donor. Using the cycle threshold (Ct) obtained by qRT-PCR, the recoveries for the 10 kDa-100 kDa filter columns were calculated based on the 3 kDa Ct values that were set at 100%. Based on these results, retention of endogenous RNA was dependent on both the donor and the transcript, with all pore sizes above 3 kDa demonstrating significantly reduced efficiency. The average retention for pore sizes 10 kDa-100 kDa for transcript 1 ranged from 32%-47% and 16%-31% for transcript 2. The results are shown in Table 5 below.

TABLE 5

Recovery of endogenous urine RNA using filter column membranes with different pore sizes.

| Donor | Transcript 1 | | | | | Transcript 2 | | | | |
|---|---|---|---|---|---|---|---|---|---|---|
| | 3 kDa | 10 kDa | 30 kDa | 50 kDa | 100 kDa | 3 kDa | 10 kDa | 30 kDa | 50 kDa | 100 kDa |
| 1 | 100% | 66% | 59% | 79% | 43% | 100% | 25% | 39% | 36% | 9% |
| 2 | 100% | 67% | 69% | 79% | 59% | 100% | 47% | 40% | 50% | 19% |
| 3 | 100% | 40% | 43% | 24% | 25% | 100% | 28% | 28% | 9% | 12% |
| 4 | 100% | 26% | 20% | 10% | 4% | 100% | 26% | 25% | 12% | 8% |
| 5 | 100% | 38% | 24% | 34% | 28% | 100% | 27% | 11% | 13% | 31% |
| Avge | 100% | 47% | 43% | 45% | 32% | 100% | 31% | 29% | 24% | 16% |

Example 4

Sample Preparation and RNA Extraction from Urine Samples

Urine sample (30 ml) was obtained from an individual with benign prostate hyperplasia was split into two 15 ml aliquots for extraction of RNA from cellular components of urine sediment and soluble urine fractions.

The first aliquot of urine was processed for RNA extraction from the cells in the urine sediment using ZR Urine RNA Isolation Kit™ (ZYMO Research Corporation). Briefly, cells were separated from urine by a syringe filter. The cells were retained on the syringe filter and the filtrate was collected separately. The retained cells were lysed directly on the filter using 700 µl of RNA Extraction Buffer Plus™ reagent (ZYMO Research Corporation) and the cell lysate was collected in a 1.5 ml tube. The cell lysate was mixed with an equal volume of ethanol and passed through Zima-Spin IC™ column. The column was washed with 300 µl of RNA Wash Buffer. Total RNA was eluted from the column by applying 25 µl of the supplied RNA Elution Buffer directly to the column membrane followed by centrifugation.

The filtrate collected from the syringe filtration step described above was further concentrated using Amicon Ultra-15, nominal molecular weight limit of 3 kDa (Millipore, Mass., USA) to a final filtrate volume of 500 µl (soluble urine concentrate), representing approximately a 30-fold concentration. The total nucleic acid was extracted from the soluble urine concentrate using NucliSENS® easy-MAG® (bioMérieux, Inc., NC, USA) using manufacturer's protocol. Briefly, total nucleic acid binds to NucliSENS® magnetic silica particles. The magnetic silica particles were separated from the liquid portion using a magnetic field. The nucleic acid bound to silica particles were washed with the wash buffer provided by the manufacturer. The nucleic acid is finally released from the solid phase with the elution buffer. FIG. 1 (pathways 1 and 2) shows a schematic of the experimental design used to process the first urine aliquot (ultrafiltration step not shown).

The second urine aliquot (15 ml) was directly applied to an Amicon Ultra-15, having a nominal molecular weight limit of 3 kDa (Millipore, Mass., USA). The urine sample was concentrated to 500 µl. The total nucleic acid was extracted from the soluble urine concentrate using NucliSENS® easy-MAG® (bioMérieux, Inc., NC, USA) using manufacturer's protocol as discussed above. FIG. 1 (pathway 3) shows a schematic of the experimental design used to process the second urine aliquot (ultrafiltration step not shown).

Example 5 cDNA Synthesis and RT-PCR cDNA Synthesis and RT-PCR were performed in a one-step process using RNA UltraSense® one-step real-time (RT) PCR System (Invitrogen): First, RNA was treated with DNase to eliminate DNA using RNA-free (Ambion). A master mix was prepared with following components for each reaction: RNA UltraSense Enzyme Mix 2.5 RNA UltraSense 5× Reaction Mix 10 µl, Taqman probe primer pair (10 µM concentration each) 1 µl, Fluorogenic probe (10 µM) 1 µl, ROX Reference Dye 1 µl. Next, 3 µl of RNA template in 31.5 µl of DEPC-treated water per reaction was added to a clean microcentrifuge tube. The 34.5 µl of template was added to the 15.5 µl of Master mix for a total of 50 µl for each reaction. After gentle mixing, the reaction mixture was subjected to brief centrifugation, and was placed in a preheated programmed thermal cycler. The instrument was programmed to perform cDNA synthesis immediately followed by PCR amplification using the following cycling parameters: 50° C. for 15 minute hold, 95° C. for 2 minute hold, 40-50 cycles of: 95° C. for 15 seconds and 60° C. for 30 seconds. After cycling, the reaction was held at 4° C. until further analysis.

Example 6

Estimation of Gene Expression Levels

Expression levels of four genes: heat shock 60 kDa protein 1 (HSPD1), inosine monophosphate dehydrogenase 2 (IMPDH2), PDZ and LIM domain 5 (PDLIM5), and UDP-N-acteylglucosamine pyrophosphorylase 1 (UAP1); and five reference genes: c-abl oncogene 1, receptor tyrosine kinase (ABL1), beta actin (ACTB), beta-2 microglobulin (B2M), glyceraldehyde-3-phosphate dehydrogenase (GAPDH), and beta glucuronidase (GUSB) were evaluated using the RNA UltraSense® one-step RT-PCR System. Taqman® probes were used to monitor DNA synthesis. Fluorescent signals were measured and plotted against the number of PCR cycles. The Ct value, the point at which the fluorescence crosses the baseline threshold is measured for each gene. A lower Ct value indicates higher initial concentration of template DNA and therefore initial RNA. The Ct values for four test genes and five reference genes were determined using the RNA isolated from cells present in urine, the urine supernatant which is free of cells, and whole urine without further separation of cells. The Ct values of different genes in various samples are presented in Table 6 below.

n=32, 48 hrs n=17, >65 hrs n=12). Effects of time-to-process (i.e. time from collection to fraction separation and extraction) on RNA quantity and quality were determined by

TABLE 6

Ct values of the Genes in Different Samples

| Kit | Sample | Test Genes | | | | 5 Reference Genes | | | | |
|---|---|---|---|---|---|---|---|---|---|---|
| | | HSPD1 | IMPDH2 | PDLIM5 | UAP1 | ABL1 | ACTB | B2M | GAPDH | GUSB |
| Zymo | Urine Sediment | 29.9 | 26.7 | 31.0 | 33.3 | 32.6 | 24.6 | 25.1 | 23.1 | 30.8 |
| Amicon | Urine Supernatant | 26.0 | 26.8 | 28.3 | 31.9 | 30.7 | 23.9 | 26.5 | 22.1 | 28.8 |
| | Soluble Urine Concentrate from Whole Urine (3K) | 26.6 | 24.8 | 27.1 | 30.9 | 29.8 | 21.4 | 23.0 | 20.6 | 27.3 |
| | Soluble Urine Concentrate from Whole Urine (10K) | 29.2 | 28.2 | 30.5 | 32.8 | 33.2 | 24.6 | 27.0 | 24.4 | 30.3 |

The results in Table 6 demonstrate that the amount of RNA in whole urine is generally higher than that obtained from the cells present in urine. Additionally, the urine supernatant contains more transcript than the cells in urine sediment for the majority of the genes tested. Furthermore, the expression pattern of the five reference genes varied among the cells in urine sediment, urine supernatant (after separation of cells) and soluble urine concentrate (without separation of cells). As seen in Table 6, concentration of whole urine to form a soluble urine concentrate consistently yielded higher amounts of RNA when a membrane with smaller pore size was used (cf. MW=3 K versus MW=10 K cutoff).

A score matrix for the four test genes were created and normalized by the five reference genes. The normalized four test genes scores indicate the expression pattern of the genes are different in the different fractions of urine (Table 7).

TABLE 7

Normalized Gene Scores

| | 4-gene score normalized by reference gene indicated | | | | | |
|---|---|---|---|---|---|---|
| RNA source | AVG | ABL | ACTB | B2M | GAPDH | GUSB |
| Urine Sediment (cellular RNA) | −8.3 | 6.6 | −15.6 | −14.2 | −19.8 | 1.6 |
| Urine Supernatant (after separation of cells) | −5.1 | 6.8 | −12.1 | −4.9 | −17.1 | 1.5 |
| Soluble Urine Concentrate (without separation of cells) | −8.1 | 6.8 | −16.5 | −12.1 | −18.7 | −0.1 |

Example 7

Figure 2:
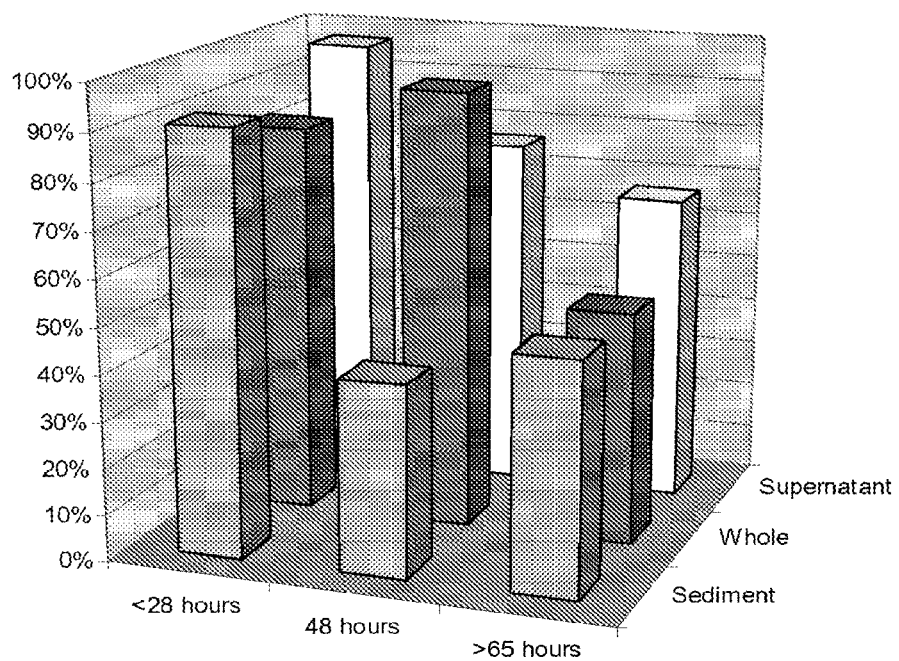
FIG. 2 is a bar graph showing the relative recovery of RNA from whole urine and the supernatant and sediment fractions, using RT-PCR, following different time-to-process delays after urine collection.

Rate of Sufficient RNA Quantity for Gene Expression Assay Based on Urine Fraction and Time-to-Process Urine samples were collected from 61 donors that were received at varying time points post collection (<28 hrs calculating the success rates of samples in each time point range. Success rates were determined by the amount of GAPDH transcript present in the RNA sample as measured by real-time RT-PCR. At <28 hours time-to-process, most samples (84-97%) yielded sufficient quantities for analysis of gene expression for all three sample types. When longer time-to-process occurred (>48 hours), urine sediment RNA is largely unsuccessful (41-50% success rate) as compare to urine supernatant and whole urine. Whole urine had a higher success rate at 48 hours (94%) than urine supernatant (76%), but urine supernatant maintained a close success rate even beyond 65 hours (67%) than whole urine (50%). See FIG. 2.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for processing urine for detection of RNA expression associated with a cancer, comprising:
    a) separating urine sediment from the soluble urine fraction of a urine sample obtained from an individual suspected of having cancer, wherein RNA associated with the cancer is present in the soluble urine fraction; and
    b) concentrating the soluble urine fraction by ultrafiltration to produce a soluble urine concentrate, wherein the volume of the soluble urine concentrate is reduced at least 50% from the original urine volume, wherein the cancer-associated RNA is selected from the group consisting of prostate cancer antigen 3 (PCA3), p antigen family, member 4 (PAGE4), solute carrier family 45, member 3 (SLC45A3), kallikrein-related peptidase, member 3 (KLK3), phosphoinositide-3-kinase, alpha polypeptide (PIK3CA), erythroblastic leukemia viral oncogene homolog 2 (ERBB2), hyaluronoglucosaminidase (HYAL1), bladder cancer associated protein (BLCAP), solute carrier family 35, member E3 (SLC35E3), tumor protein p53 (TP53), and suppressor of tumorigenicity 20 (ST20).

2. The method of claim 1, wherein the cancer is prostate cancer, ovarian cancer, bladder cancer, uterine cancer or cervical cancer.

3. The method of claim 1, wherein urine sediment is separated from the soluble urine fraction by centrifugation or filtration.

4. The method of claim 1, wherein said ultrafiltration comprises a filter having a nominal molecular weight limit of not more than about 100,000 daltons.

5. The method of claim 1, wherein said ultrafiltration comprises a filter having a nominal molecular weight limit of not more than about 50,000 daltons.

6. The method of claim 1, wherein said ultrafiltration comprises a filter having a nominal molecular weight limit of between about 3,000 daltons and about 10,000 daltons.

7. The method of claim 1, wherein said ultrafiltration comprises a filter having a nominal molecular weight limit of about 3,000 daltons.

8. The method of claim 1, wherein the RNA is isolated from the soluble urine concentrate by solid phase extraction.

9. The method of claim 1, further comprising:
    c) isolating RNA from the soluble urine concentrate produced in step (b),
    d) reverse transcribing the RNA from the soluble urine concentrate produced in step (c) to form cDNA; and
    e) amplifying the cDNA produced in step (d).

10. The method of claim 9, wherein urine sediment is separated from the soluble urine fraction by centrifugation or filtration.

11. The method of claim 9, wherein said ultrafiltration comprises a filter having a nominal molecular weight limit of not more than about 50,000 daltons.

12. The method of claim 9, wherein said ultrafiltration comprises a filter having a nominal molecular weight limit of between about 3,000 daltons and about 10,000 daltons.

13. The method of claim 9, wherein said ultrafiltration comprises a filter having a nominal molecular weight limit of about 3,000 daltons.

14. The method of claim 9, wherein the RNA is isolated from the soluble urine concentrate by solid phase extraction.

15. The method of claim 9, wherein the RNA is mammalian RNA.

16. A method for isolating nucleic acids from a urine sample for detection of RNA expression associated with a cancer, said method comprising,
    a) providing a urine sample from an individual suspected of having a cancer,
    b) processing said urine sample to produce a cell-free urine sample, wherein RNA associated with the cancer is present in the cell-free urine sample, and
    c) subjecting said cell-free urine sample to ultrafiltration using a filter having a nominal molecular weight limit of between about 3 kDa and about 100 kDa, to produce a soluble urine concentrate, wherein the RNA associated with the cancer is retained in the soluble urine concentrate, and wherein the volume of the soluble urine concentrate is reduced at least 50% from the original urine volume, wherein the benign prostate hyperplasia-associated RNA is selected from the group consisting of prostate cancer antigen 3 (PCA3), p antigen family, member 4 (PAGE4), solute carrier family 45, member 3 (SLC45A3), kallikrein-related peptidase, member 3 (KLK3), phosphoinositide-3-kinase, alpha polypeptide (PIK3CA), erythroblastic leukemia viral oncogene homolog 2 (ERBB2), hyaluronoglucosaminidase (HYAL1), bladder cancer associated protein (BLCAP), solute carrier family 35, member E3 (SLC35E3), tumor protein p53 (TP53), and suppressor of tumorigenicity 20 (ST20).

17. The method of claim 16, wherein the cancer is prostate cancer, ovarian cancer, bladder cancer, uterine cancer or cervical cancer.

18. The method of claim 16, further comprising:
    d) isolating RNA from the soluble urine concentrate produced in step (c),
    e) reverse transcribing the RNA from the soluble urine concentrate produced in step (d) to form cDNA; and
    f) amplifying the cDNA produced in step (e).

19. The method of claim 18, wherein the RNA is isolated from the soluble urine concentrate by solid phase extraction.

20. A method for processing urine for detection of RNA expression associated with a cancer comprising concentrating a urine sample from an individual suspected of having a cancer to produce a soluble urine concentrate wherein RNA associated with the cancer present in the urine sample is retained in the soluble urine concentrate, wherein the volume of the soluble urine concentrate is reduced at least 50% from the original urine volume, and wherein the cancer-associated RNA is selected from the group consisting of prostate cancer antigen 3 (PCA3), p antigen family, member 4 (PAGE4), solute carrier family 45, member 3 (SLC45A3), kallikrein-related peptidase, member 3 (KLK3), phosphoinositide-3-kinase, alpha polypeptide (PIK3CA), erythroblastic leukemia viral oncogene homolog 2 (ERBB2), hyaluronoglucosaminidase (HYAL1), bladder cancer associated protein (BLCAP), solute carrier family 35, member E3 (SLC35E3), tumor protein p53 (TP53), and suppressor of tumorigenicity 20 (ST20).

\* \* \* \* \*